United States Patent [19]

Szejtli et al.

[11] Patent Number: 4,923,853
[45] Date of Patent: May 8, 1990

[54] PROCESS FOR ENHANCING THE ACTIVITY OF PLANT PROTECTING AGENTS BY USING CYCLODEXTRIN

[75] Inventors: József Szejtli; Péter Tétényi; Márta Kiniczky; Jenö Bernáth; Magda Tétényi née Erdösi; Éva Dobos; Erzsébet Bánky née Elöd, all of Budapest, Hungary

[73] Assignee: Chinoin Gyogyszer Es Vegyeszeti Termekek Gyara R.T., Budapest, Hungary

[21] Appl. No.: 218,466

[22] Filed: Jul. 11, 1988

Related U.S. Application Data

[63] Continuation of Ser. No. 916,484, filed as PCT HU86/00001 on Jan. 7, 1986, published as WO86/03439 on Jul 17, 1986, abandoned.

[30] Foreign Application Priority Data

Jan. 7, 1985 [HU] Hungary .................................. 41/85

[51] Int. Cl.$^5$ ..................... A01N 43/04; A01N 9/00; A61K 31/715
[52] U.S. Cl. ..................................................... 514/58
[58] Field of Search ........................... 424/405; 514/58

[56] References Cited

U.S. PATENT DOCUMENTS 3,846,551 11/1974 Mifune et al. ..................... 514/58
4,524,068 6/1985 Szejtli et al. ..................... 514/58

OTHER PUBLICATIONS

Chem. Abstracts, vol. 94, Entry 115997, Nov. 1980.
Chem. Abstracts, vol. 103, Entry 174021t, Apr. '85.
Merck Index 10th Edition, Compound 7351, p. 1078.

*Primary Examiner*—Joseph L. Schofer
*Assistant Examiner*—Peter F. Kulkosky
*Attorney, Agent, or Firm*—Herbert Dubno; Jonathan Myers

[57] ABSTRACT

The invention relates to fungicidal plant protecting composition comprising 3–90% by weight of a fungicidal active ingredient in admixture with 1–90% by weight of cyclodextrin and optionally with usual auxiliary agents.

The advantage of the synergistic composition of the present invention is that identical fungicidal effect can be achieved with a significantly lower active ingredient dosage and this decreases the costs involved with the active ingredient and reduces the risks of environmental pollution as well.

9 Claims, No Drawings

PROCESS FOR ENHANCING THE ACTIVITY OF PLANT PROTECTING AGENTS BY USING CYCLODEXTRIN

This is a continuation of co-pending application Ser. No. 916,484 filed as PCT HU86/00001 on Jan. 7, 1986, published as WO86/03939 on Jul. 17, 1986, now abandoned.

TECHNICAL FIELD

This invention relates to new and improved plant protecting agents, particularly fungicidal compositions and a method for the use thereof.

BACKGROUND ART

Recently several articles and patents have been published relating to the use of cyclodextrin in plant protecting formulations [Növényvédelem, 19, 364 (1983); J. Szejtli: Cyclodextrins and their Inclusion Complexes, Akadémiai Kiadó, Budapest, 1982]. On forming complexes of molinate (S-ethyl-N,N-hexamethylene-thiocarbamate), bentiocarb (S-4-chlorobenzyl-diethylthio carbamate) and dichlorphos (2,2-dichlorovinyl-dimethyl-phosphate) the volatility of the active ingredient is significantly decreased and the activity of the pesticide remains sufficient for a longer period of time [Mikasa Chemical Industrial Co; KOKAI No. 80.81806; DOS No. 2,422,316 (1974); Acta Chem. Acad. Sci. Hung. 107, 195 (1981)]. Methylparathion (0,0-dimethyl-0-4-nitrophenyl-phosphorothioate) and natural pyrethrines and pyrethroides, respectively, are converted into the cyclodextrin A 3673/77-OE complexes in order to increase the stability against light and oxygen to a considerable extent [Pestic. Sci. 11, 134 (1980); U.S. Pat. No. 3,846,551 (1974);Nippon Noyaku Gakkaishi 1, 41 (1976); 2, 41 (1977)]. The dichlobenyl (2,6-dichloro-benzonitrile) active ingredient easily sublimates and on standing the granulated product sticks together; this can be inhibited by forming complex with cyclodextrin [5th Int. Cong. Pesticide Chem. (IUPAC) Kyoto (1983)].

The complex formation of 2-chloromethane-phosphonic acid with cyclodextrin results in the fact that on contacting with plant tissue the ethylene release is a long-lasting process and this is more efficient than the delivery of ethylene from a very promptly acting active ingredient [Acta Chim. Acad. Sci. Hung. 107, 231 (1981)].

DISCLOSURE OF THE INVENTION

It was not aforeseen from the prior art that cyclodextrin would synergize the efficiency of fungicides.

The object of the present invention is to provide fungicidal compositions comprising cyclodextrin in which cyclodextrin synergizes the activity of known fungicidal active ingredients to a significant extent. Thus identical fungicidal active ingredient dosage results in a higher activity or the same fungicidal effect can be achieved by using a lower dose of the active ingredient and this is a considerable advantage from the point of view of both economy and the safety of environment.

According to an aspect of the present invention there is provided a fungicidal plant protecting composition comprising 3-90% by weight of a fungicidal active ingredient in admixture with 1-90% by weight of cyclodextrin and optionally with usual auxiliary agents.

In the fungicidal composition according to the present invention the ratio of the fungicidal active ingredient and cyclodextrin amounts to 90:1–1:5, preferably 2–5:1.

The composition according to the present invention may preferably comprise the following fungicidal active ingredients:

benomyl = 1-butylcarbamoyl-benzimidazole-2-methyl-carbamate;
BCM = 2-carbomethoxyamino-benzimidazole;
metomeclan = 1-(3,5dichlorophenyl)-3-methoxy-methyl-pyrrolidine-2,5-dione;
phenarimol = 2,4'-dichloro-α-(pyrimidine-5-yl)--diphenyl-methanol.

As cyclodextrin α-, β- and/or γ-cyclodextrin may be used.

According to a preferable embodiment of the present invention the ratio of the above active ingredients and cyclodextrin may be as follows:
benomyl:cyclodextrin = 2–5:1
BCM:cyclodextrin = 2–5:1
metomeclan:cyclodextrin = 2–20:1
phenarimol:cyclodextrin = 1–100:10.

According to a further aspect of the present invention there is provided a fungicidal method of treatment which comprises applying onto the plants or the other surface to be treated a composition according to the present invention, preferably at a rate of 0.5–6 kg/ha, particularly 1.2–1.6 kg/ha.

The present invention is based on the recognition that known fungicidal active ingredients and cyclodextrin exhibit a synergistic effect which is a result of one or two of the following factors:
the fungistatical activity of cyclodextrins themselves;
the solubility increasing effect of cyclodextrins.

The fungistatical activity of cyclodextrins has never been disclosed in prior art. The said activity may be proved by the following test:

Agar nutrient media comprising 0.1-0.2-0.5-1.0-2.0-5.0-10.0-20.0-100.0-200.0-400.0-800.0-1200.0-1500.0-2000.0-3000.0 μg β-cyclodextrin/ml, respectively, are prepared in Petri-dishes. Mycelium discs are cut out from surface cultures of three test fungi and are placed onto the agar nutrient media in the Petri-dishes. Incubation is carried out in a thermostate whereupon the increase of the diameter of the colonies is determined and compared to that of the control. The morphology of the colonies and the diffusion of the dye-substance produced by the fungi into the nutrient medium are evaluated as well. The results are summarized in Table 1.

TABLE 1

| | Fungistatical effect of β-cyclodextrin | | |
| --- | --- | --- | --- |
| | Inhibition % | | |
| | Microorganisms | | |
| Concentration | Rhizoctonia solani | Sclerotinia sclerotiorum | Alternaria tenuis |
| 3000 | 19 | 16 | 14 |
| 1500 | 17 | 14 | 12 |
| 400 | 6 | 12 | 10 |
| 200 | 3 | 12 | 7 |

In a dose range of 0.1–20 μg/ml the effect of β-cyclodextrin is of a qualitative character. The fungistatical effect of cyclodextrin manifests itself in the changed morphology, structure and color of the colonies and in the amount of the dyestuff penetrated into the nutrient medium. However at higher dose range the effect of cyclodextrin is already of a quantitative nature, thus the decrease of the diameter of the colonies can be measured and the amount of the biomass formed is reduced to a rate which can be evaluated (Table 1). A study of the surfacial cultures show that β-cyclodextrin inhibits the formation of the propagative organs.

The main feature of the solubility increasing effect of cyclodextrin due to the formation of inclusion complexes resides in the fact that in aqueous solution beside the molecularly dispersed (i.e. actually dissolved) active ingredient and the mycelia consisting of some or a lot of molecules (microcrystal, microdrop), the cyclodextrin-active ingredient inclusion complex being also in molecularly dispersed form appears, too.

Since the said system is characterized by an unusually dynamical equilibrium (within $10^{-8}$ sec$^{-1}$) the active ingredient incorporated into the inclusion complex acts in the same way from the point of view of absorption as the free dissolved active ingredient.

Thus the concentration of molecularly dispersed molecules being suitable for direct absorption may be significantly increased with the aid of cyclodextrins and this accelerates the rate of absorption, i.e. the same efficiency can be achieved by using a lower active ingredient dose.

The positive effect of cyclodextrin on the solubility of active ingredients is shown on the example of benomyl. The said active ingredient (1-butylcarbamoyl-benzimidazole-2-methyl-carbamate) is a systemic fungicide, which is poorly soluble in water and when dissolved in water rapidly decomposes to methyl-benzimidazole carbamate having also a fungicidal effect but being still less soluble in water.

On shaking benomyl and benomyl+cyclodextrin, respectively, in water at 25° C. the solubility data summarized in Table 2 are obtained. (Benomyl and benomyl+β-cyclodextrin, respectively, are shaken in water at 25° C., the samples are filtered and the dissolved benomyl contents of the filtrates are determined by UV spectrophotometry).

TABLE 2

| Time of experiment (minutes) | Increase of the solubility of benomyl under the effect of β-cyclodextrin | | | |
|---|---|---|---|---|
| | Amount of dissolved benomyl | | | |
| | μg/ml | % | μg/ml | % |
| | Weighed in: 1000 μg/ml of benomyl | | Weighed in: 170 μg of benomyl + 830 μg/ml of β-CD | |
| 10 | 2 | 0.2 | 7 | 4.1 |
| 20 | 3 | 0.3 | 9 | 5.3 |
| 40 | 4.5 | 0.45 | 10 | 5.9 |
| 80 | 5 | 0.5 | 12 | 7.0 |
| 120 | 5 | 0.5 | 13 | 7.6 |
| | Weighed in: 5000 μg/ml of benomyl | | Weighed in: 850 μg of benomyl + 4150 μg/ml β-CD | |
| 10 | 3.5 | 0.07 | 12 | 1.4 |
| 20 | 4 | 0.08 | 16 | 1.9 |
| 40 | 6 | 0.12 | 17 | 2.0 |
| 80 | 8 | 0.16 | 18 | 2.1 |
| 120 | 9.5 | 0.19 | 19 | 2.2 |

Benomyl is put on the market under the commercial name Fundazol 50 WP; benomyl active ingredient content: 50%. In Table 3 the solubility data of benomyl, a mixture of benomyl and cyclodextrin, Fundazol 50 WP, and a mixture of Fundazol 50 WP and cyclodextrin are shown. In each experiment 3000 μg/ml of the test substance are weighed in and shaken at 25° C. Benomyl is a 100% active ingredient; the benomyl content of the benomyl/cyclodextrin mixture amounts to 17.3%; the benomyl content of Fundazol 50 WP is 50%; the benomyl content of the mixture of Fundazol 50 WP and cyclodextrin amounts to 8.65%. It appears from Table 3 that as a result of the formulation the solubility of benomyl is increased four times.

Cyclodextrin per se causes a further 1.5-2-fold increase of the solubility of both original benomyl and formulated Fundazol 50 WP. Taking into consideration that in the mixtures comprising cyclodextrin the amount of benomyl active ingredient is considerably lower and at the same time in aqueous solution the concentration of benomyl being responsible for the actual biological effect became significantly higher, it was aforeseen that this had to be manifested in the biological effect, too.

TABLE 3

| Increase of the solubility of benomyl from Fundazol under the effect of β-cyclodextrin | | | | |
|---|---|---|---|---|
| Time of experiment (minutes) | Dissolved benomyl (μg/ml) | | | |
| | Benomyl | Benomyl + BCD | Fundazol | Fundazol + BCD |
| 10 | 2 | 5 | 27 | 40 |
| 20 | 5 | 8 | 28 | 42 |
| 40 | 6 | 11 | 29 | 44 |
| 80 | 7 | 13 | 30 | 46 |
| 120 | 8 | 13 | 31 | 48 |
| 160 | 9 | 13 | 32 | 49 |

The solubility of benomyl from various materials comprising benomyl was determined by shaking in water at 25° C. 2000 μg/ml of solid material are weighed in which corresponds to the following amounts of benomyl:

in the case of benomyl: 2000 μg/ml in the case of benomyl+β-CD: 350 μg/ml++1650 μg β-CD in the case of Fundazol 50 WP: 1000 μg/ml in the case of Fundazol 50 WP+β-CD: 175 μg/ml++1650 μg β-CD.

The following tests substantiate the surprising synergism between known fungicides and β-cyclodextrin. Stable, highly dispersed aqueous suspensions of the test materials are added to agar nutrient media in the desired concentration (0.1-200 μg/ml), whereupon the nutrient media are poured into Petri-dishes. Mycelium discs are cut out from the surfacial cultures of the test fungi and the discs are placed into the Petri-dishes containing the test materials. Incubation is carried out in thermostate whereupon the increase of the diameter of the colonies is measured and and compared to that of the control. The tests are carried out in three replicates.

In Table 4 the effect of the fungicide Fundazol 50 WP (benomyl content 50%) and a mixture of Fundazol 50 WP+10% of β-cyclodextrin is disclosed. The results clearly prove the synergistic activity of β-cyclodextrin; the increased activity is particularly significant against Botrytis cinerea and Monilia fructigena.

TABLE 4

| Fungicidal activity of Fundazol and recrystallized β-cyclodextrin | | | |
|---|---|---|---|
| | $ED_{50}$ (μg/ml, related to active ingredient) | | |
| Microorganism | Fundazol | Fundazol + 10% β-CD | Increase of activity (x) |
| Rhizoctonia solani | 0.87 | 0.64 | 1.3 |
| Sclerotinia sclerotiorum | 0.12 | 0.05 | 2.4 |
| Fusarium moniliforme | 0.88 | 0.38 | 2.3 |

TABLE 4-continued

Fungicidal activity of Fundazol and recrystallized β-cyclodextrin

| Microorganism | ED$_{50}$ (μg/ml, related to active ingredient) | | Increase of activity (x) |
|---|---|---|---|
| | Fundazol | Fundazol + 10% β-CD | |
| Botrytis cinerea | 0.14 | 0.0125 | 10.2 |
| Ascochyta pisi | 0.72 | 0.25 | 2.9 |
| Fusarium culmorum | 0.77 | 0.44 | 1.7 |
| Colletotrichum lini | 0.68 | 0.5 | 1.3 |
| Monilia fructigena | 0.05 | 0.0125 | 4.0 |

Metomeclan is a contact fungicide insoluble in water [1-(3,5-dichlorophenyl)-3-methoxymethyl-pyrrolidine-2,5-dione]. The activity of metomeclan is significantly increased by the addition of cyclodextrin. In Table 5 the fungicidal effect of metomeclan and a mixture of metomeclan +10% of β-CD is set forth.

TABLE 5

Increase of activity of metomeclan Additional adding 10% of β-cyclodextrin

| Test microorganism | ED$_{50}$ (μg/ml, related to active ingredient) | | Increase of activity (x) |
|---|---|---|---|
| | Metomeclan | Metomeclan + 10% of β-CD | |
| Fusarium moniliforme | 12 | 7 | 1.7 |
| Alternaria tennis | 2.9 | 1.8 | 1.6 |
| Stemphylium radicinum | 5.7 | 3.9 | 1.5 |
| Rhizoctonia solani | 3.3 | 2.3 | 1.4 |
| Colletotrichum lini | 25.5 | 8.9 | 2.9 |
| Ascochyta pisi | 4.6 | 2.8 | 1.6 |
| Fusarium culmorum | 16.5 | 7.5 | 2.2 |
| Alternaria crassa | 3.9 | 2.2 | 1.8 |

In vivo tests are carried out on wheat-powdery mildew (host-parasite) by using a combination of phenarimol [2,4'-dichloro-α--(pyrimidine-5-yl)-diphenyl-ethanol] and β-cyclodextrin. The tests are carried out in three replicates in phytotrone under usual experimental system and environmental conditions (20° C., humidity 90%, light intensity 9000 lux.) In culturing dishes (diameter 11 cm) as average 160 plants (5–6 cm stage) are treated with 8 ml of stable aqueous suspensions comprising the test material. The results are summarized in Table 6. The inhibition activity is calculated on the basis of the Hinfner-Papp formula by using the infectedness index.

TABLE 6

In vivo test of phenarimol + β-cyclodextrin on wheat powdery mildew host parazite

| Phenarimol concentration μg/ml | Inhibition activity % | |
|---|---|---|
| | Phenarimol | Phenarimol + β-CD (ratio 1:5) |
| 10 | 100.0 | 100.0 |
| 5 | 99.4 | 100.0 |
| 2.5 | 87.2 | 98.2 |
| 1.25 | 73.5 | 83.2 |
| 0.625 | 29.4 | 42.3 |

In a further series of experiments it is tested whether known linear dextrins obtained by thermal, enzymatic or acidic decomposition of starch exhibit similar effects as cyclodextrins. The said tests show unambiguously that only cyclodextrins possess the above fungicidal-synergizing activity.

INDUSTRIAL APPLICABILITY

As a result of the synergizing effect of cyclodextrins the dosage of known and generally used fungicidal active ingredients can be significantly decreased under achieving identical or even increased fungicidal effect and this decreases the costs involved with the active ingredients and reduces the risks of environmental pollution as well.

MODES OF CARRYING OUT THE INVENTION

Further details of the present invention are to be found in the following Examples without limiting the scope of protection to the said Examples.

EXAMPLE 1

Spray Comprising Benomyl As Active Ingredient

Benomyl is put on the market as spray in the form of a wettable powder having an active ingredient content of 50% under the commercial name Fundazol 50 WP. A product having the same activity but containing a smaller amount of active ingredient is prepared as follows:

35 kg of benomyl pre-micronized in an air-flow mill and 15 kg of crystalline β-cyclodextrin (moisture content 13%) also pre-micronized in an air-flow mill are admixed with 40 kg of precipitated calcium carbonate, 5 kg of sulfide waste powder and 5 kg of an anionic tenside containing 50% of water (preferably Genapol PGM, pre-heated to 50° C.) in a homogenizer. The homogenized material is dried, micronized in order to separate the particles stocked together and finally packed.

EXAMPLE 2

One proceeds according to Example 1 i.e. the components are micronized, homogenized, dried and re-micronized. The composition is as follows:

| | |
|---|---|
| Benomyl (related to 100% active ingredient) | 40 kg |
| Precipitated calcium carbonate | 40 kg |
| Tensiofix BC$_2$ | 2.5 kg |
| Totamine | 5 kg |
| β-Cyclodextrin | 12.5 kg |

EXAMPLE 3

Seed-Treating Composition Comprising Benomyl As Active Ingredient

One proceeds according to Example 1. The composition is as follows:

| | |
|---|---|
| Benomyl | 35 kg |
| Diotilan | 1 kg |
| Evidet 27 | 1 kg |
| Tylose N 20 | 1 kg |
| Aerosil "300" | 0.5 kg |
| Safranin P extra | 2 kg |
| Spray-dried crude converted cyclodextrin mixture (β-cyclodextrin content about 48%; α- and γ -cyclodextrin content 2%, partially decomposed starch content about 50%) | 38 kg |
| Precipitated calcium carbonate | 21.5 kg |

EXAMPLE 4

Seed-Treating Composition Comprising Abem (2-Carbomethoxyaminobenzimidazole) As Active Ingredient The Abem active ingredient is dissolved in hydrochloric acid under heating, whereupon it is neutralized with an emulsion consisting of a mixture of ammonium hydroxide, paraffin oil and β-cyclodextrin. The suspension is stabilized with tensides in a manner known per se. The seed-treating agent has the following composition:

| | |
|---|---|
| Abem | 15% |
| Paraffin oil | 19.8% |
| β-cyclodextrin | 5% |
| Ethylene glycol | 5.6% |
| Ammonium chloride (formed on neutralizing the hydrochloric acid solution) | about 10% |

Various tensides:

| | |
|---|---|
| Emulsogen M | 0.24% |
| Atlox 4868 B | 1.6% |
| Triton X 45 | 1.9% |
| Tensiofix L 051 | 0.2% |
| Tensiofix 821 | 0.2% |
| filled up with water to | 100% |

What we claim is:

1. A fungicidal plant-protecting composition which consists essentially of:
   (a) a fungicidally active ingredient selected from the group consisting of benomyl, BCM and metomeclan; and
   (b) a cyclodextrin selected from the group consisting of alpha-cyclodextrin, beta-cyclodextrin, and gamma-cyclodextrin, wherein the weight ratio between the fungicide and the cyclodextrin is 49:1 to 7:3, together with a fungicidally acceptable inert carrier.

2. The fungicidal plant-protecting composition according to claim 1 wherein the fungicidally active ingredient is benomyl and the weight ratio of the benomyl to the cyclodextrin is 5:1 to 7:3.

3. The fungicidal plant-protecting composition according to claim 1 wherein the fungicidally active ingredient is BCM and the weight ratio of the BCM to the cyclodextrin is 5:1 to 7:3.

4. The fungicidal plant-protecting composition according to claim 1 wherein the fungicidally active ingredient is metomeclan.

5. The fungicidal plant-protecting composition according to claim 1 wherein the fungicidally active ingredient is benomyl, the cyclodextrin is beta-cyclodextrin and the weight ratio of the benomyl to the cyclodextrin is about 4.5:1.

6. The fungicidal plant-protecting composition according to claim 1 wherein the fungicidally active ingredient is BCM, the cyclodextrin is beta-cyclodextrin and the weight ratio of the BCM to the cyclodextrin is about 3:1.

7. The fungicidal plant-protecting composition according to claim 1 wherein the fungicidally active ingredient is metomeclan, the cyclodextrin is beta-cyclodextrin and the weight ratio of the metomeclan to the cyclodextrin is about 10:1.

8. A fungicidal method of treatment which comprises the step of applying to a plant site in need of fungicidal treatment, a fungicidally effective amount of the fungicidal composition defined in claim 1.

9. The fungicidal method of treatment defined in claim 8 wherein the fungicidal composition is applied at a rate of 1.2 to 1.6 kg/ha.

* * * * *